(12) United States Patent
Wei et al.

(10) Patent No.: US 10,781,160 B1
(45) Date of Patent: Sep. 22, 2020

(54) HEXADECYL TREPROSTINIL CRYSTALS AND METHODS FOR PREPARATION THEREOF

(71) Applicant: CHIROGATE INTERNATIONAL INC., Yangmei (TW)

(72) Inventors: Shih-Yi Wei, Yangmei (TW); Jian-Bang Jheng, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/592,835

(22) Filed: Oct. 4, 2019

(51) Int. Cl.
C07C 69/736 (2006.01)
C07C 67/52 (2006.01)

(52) U.S. Cl.
CPC ............ *C07C 69/736* (2013.01); *C07C 67/52* (2013.01); *C07B 2200/13* (2013.01); *C07C 2603/14* (2017.05)

(58) Field of Classification Search
CPC ... C07C 69/736; C07C 67/52; C07C 2603/14; C07B 2200/13

USPC ......................................................... 560/56
See application file for complete search history.

(56) References Cited

U.S. PATENT DOCUMENTS

2015/0148414 A1   5/2015  Malinin et al.
2017/0320813 A1  11/2017  Malinin et al.

OTHER PUBLICATIONS

Richard W. Chapmana, et al.: Inhaled hexadecyl-treprostinil provides pulmonary vasodilator activity at significantly lower plasma concentrations than infused treprostinil: Pulmonary Pharmacology & Therapeutics 49 (2018) 104-111, Drug Research, 68. 605-614.
Franziska G. Leifer, et al.: Inhaled Treprostinil-Prodrug Lipid Nanoparticle Formulations Provide Long-Acting Pulmonary Vasodilation Drug Res 2018: 68: 605-614.

*Primary Examiner* — Deborah D Carr
(74) *Attorney, Agent, or Firm* — Ladas & Parry LLP

(57) ABSTRACT

There is provided stable crystalline Form I and Form II of Hexadecyl Treprostinil ($C_{16}TR$) and processes for the preparation thereof. The stable crystalline Form I and Form II of Hexadecyl Treprostinil present advantages in storage, formulation, shipment and handling for commercially considerations.

18 Claims, 6 Drawing Sheets

HEXADECYL TREPROSTINIL CRYSTALS AND METHODS FOR PREPARATION THEREOF

FIELD OF THE INVENTION

The present invention relates in general to solid forms of prostacyclin derivatives and in particular, to solid crystalline forms of Hexadecyl Treprostinil and preparation methods thereof.

BACKGROUND OF THE INVENTION

Hexadecyl Treprostinil ($C_{16}TR$) is a synthetic benzoprostacyclin analogue as the prodrug of Treprostinil. The structures of Treprostinil and Hexadecyl Treprostinil are shown in the following Scheme A. Hexadecyl Treprostinil is of great importance from a pharmacologically point of view. The inhaled Hexadecyl Treprostinil formulated in lipid nanoparticles is a long acting pulmonary vasodilator providing significantly lower plasma concentrations than infused Treprostinil (Tyvaso®) for treating pulmonary arterial hypertension (PAH), and can be applied for less toxicity, better tolerability and more convenient dosing schedules, e.g., *Pulm. Pharmacol. Ther.,* 49, 104-111, *Drug Research,* 68, 605-614, and US 2015/148414.

Scheme A

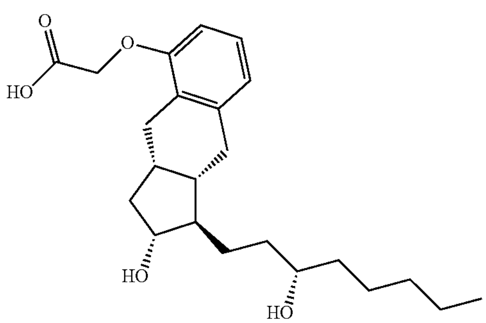

Treprostinil

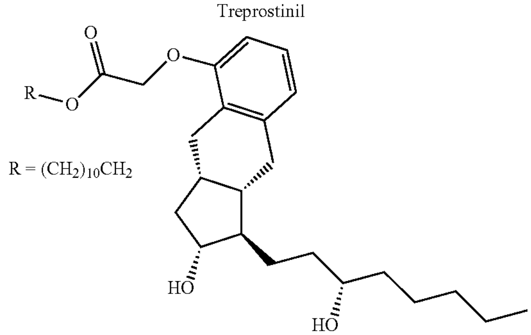

R = $(CH_2)_{10}CH_2$

Hexadecyl Treprostinil

The synthesis processes of Hexadecyl Treprostinil had been disclosed by *Drug Research,* 68, 605-614 and US 2017/0320813. However, these reports revealed that the prepared Hexadecyl Treprostinil is an off-white waxy solid. It is well known that a waxy solid is an amorphous form of active pharmaceutical ingredients (API). The thermal stability, purity and homogeneity of an amorphous API are not satisfactory comparing to a crystalline one. Besides, a waxy solid is usually provided with high viscosity, and is difficult for commercially handling to avoid sticking lost on container. Since there is no other report disclosing the crystalline form of Hexadecyl Treprostinil, the benefits of the conventional crystallization methods for preparing a stable Hexadecyl Treprostinil crystal cannot be evaluated based on the prior art reference.

Consequently, there is an urgent demand for the preparation of a stable crystalline form of Hexadecyl Treprostinil. A stable Hexadecyl Treprostinil crystal having fixed physicochemical properties can provide constant operating parameters, e.g., solubility for regular pharmaceutical formulation and steady bioabsorbability for pharmacological treatment. Additionally, a stable Hexadecyl Treprostinil crystal can also present advantages in storage, formulation, handling and shipment and for commercially considerations.

SUMMARY OF THE INVENTION

According to one aspect, the present invention provides a stable solid form of Hexadecyl Treprostinil crystal Form I, and processes for the preparation thereof.

In one embodiment, the present invention provides a method for preparing a crystalline Form I of Hexadecyl Treprostinil, which comprises dissolving Hexadecyl Treprostinil in a first solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution; lowering the temperature and/or adding a second solvent selected from the group consisting of acetonitrile, water, and mixtures thereof to the homogenous solution; and stirring until a precipitate is formed.

In one embodiment, the present invention provides a crystalline Form I of Hexadecyl Treprostinil having an X-ray powder diffraction (XRPD) pattern exhibiting its six strongest characteristic peaks at the following 2θ reflection angles: 3.3±0.2°, 6.6±0.2°, 14.2±0.2°, 18.9±0.2°, 21.3±0.2°, and 22.5±0.2°.

In one embodiment, the present invention provides a crystalline Form I of Hexadecyl Treprostinil having a differential scanning calorimetry (DSC) thermogram pattern comprising an endothermic peak with a peak onset temperature of approximately 52.2±1° C. and a peak maximum of approximately 54.5±1° C.

According to one aspect, the present invention provides a stable solid form of Hexadecyl Treprostinil crystal Form II, and processes for the preparation thereof.

In one embodiment, the present invention provides a method for preparing a crystalline Form II of Hexadecyl Treprostinil, which comprises dissolving Hexadecyl Treprostinil in a third solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution; lowering the temperature and/or adding a fourth solvent selected from the group consisting of pentane, hexane, heptane, octane, nonane, decane, cyclopentane, cyclohexane, cycloheptane, and mixtures thereof to the homogenous solution; and stirring until a precipitate is formed.

In one embodiment, the present invention provides a crystalline Form 11 of Hexadecyl Treprostinil having an XRPD pattern exhibiting its six strongest characteristic peaks at the following 2θ reflection angles: 3.41±0.2°, 6.1±0.2°, 9.4-0.2°, 20.3±0.2°, 21.6±0.2°, and 23.4±0.2°.

In one embodiment, the present invention provides a crystalline Form II of Hexadecyl Treprostinil having a DSC thermogram pattern comprising an endothermic peak with a peak onset temperature of approximately 54.6±1° C. and a peak maximum of approximately 56.9±1° C.

The present invention provides solid forms of Hexadecyl Treprostinil crystal Form I and Form II, which can stable storage at room temperature without crystalline form transformation for commercially handling.

DETAILED DESCRIPTION OF THE INVENTION

Figure 1:
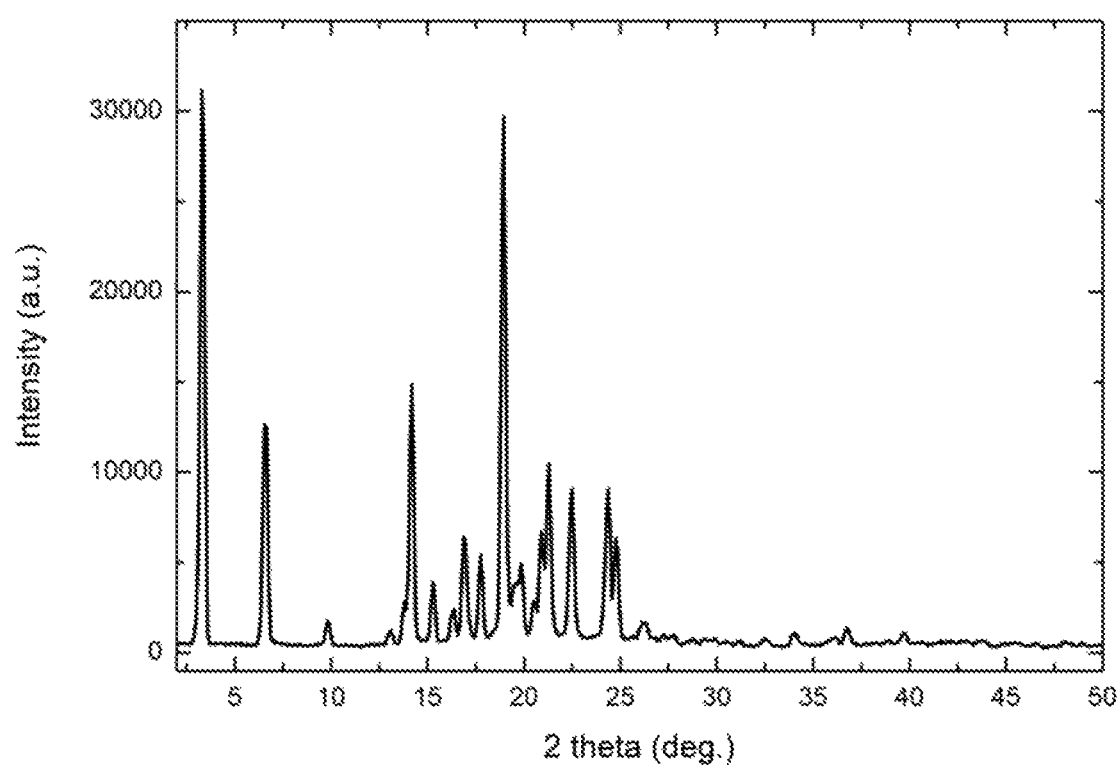
FIG. 1 shows an X-ray powder diffraction (XRPD) pattern of Hexadecyl Treprostinil crystal Form I.

Hexadecyl Treprostinil Crystal Form I and Preparation Thereof

In an embodiment of the present invention, the method for preparing Hexadecyl Treprostinil crystal Form I comprises the steps of:
(a) dissolving crude Hexadecyl Treprostinil in a first solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution;
(b) lowering the temperature and/or adding a second solvent selected from the group consisting of acetonitrile, water, and mixtures thereof to the homogeneous solution;
(c) stirring until a precipitate is formed;
(d) filtering out the precipitate thereby isolating the Hexadecyl Treprostinil crystal Form I; and
(e) optionally drying the Hexadecyl Treprostinil crystal Form I.

In the present invention, the first solvent used to dissolve the crude Hexadecyl Treprostinil is selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof, preferably ethanol and propanol. The volume of the first solvent depends on the types of the solvents used and may be about 0.5 ml to about 100 ml, preferably about 1 ml to about 50 ml, and more preferably about 2 ml to about 20 ml or about 5 ml to about 10 ml, per 1 g of the crude Hexadecyl Treprostinil. The crude Hexadecyl Treprostinil can be dissolved in the first solvent at a temperature ranging from about 0° C. to about 80° C., preferably from about 10° C. to so about 60° C., and more preferably from room temperature to about 40° C.

In one embodiment of the present invention, the temperature of the homogenous solution is lowered to a temperature ranging from about −30° C. to about 50° C., preferably from about −20° C. to about 40° C., and more preferably from about −10° C. to about 30° C.

The selection of the second solvent is the key to determine whether a Hexadecyl Treprostinil crystal Form I can be formed. In a preferred embodiment, the volume of the second solvent selected from the group consisting of acetonitrile, water, and mixtures thereof depends on the types of the solvents used and may be about 0.5 ml to about 200 ml, about 1 ml to about 150 ml, or about 2 ml to about 100 ml, per 1 ml of the first solvent. The second solvent can be added at a temperature ranging from about −30° C. to about 50° C., preferably from about −20° C. to about 40° C., and more preferably from about −10° C. to about 30° C.

In one embodiment of the present invention, the precipitation of the crystal may be performed at a temperature ranging from about −30° C. to about 50° C., preferably from about −20° C. to about 40° C., and more preferably from about −10° C. to about 30° C.

In one embodiment of the present invention, the step of filtering out the precipitate comprises using the second solvent or a mixture of the first solvent and the second solvent to wash the precipitate. In the mixing solvent, the ratio of the first solvent and the second solvent may be about 1:1 to about 1:100, preferably about 1:10 to about 1:50.

In one embodiment of the present invention, the Hexadecyl Treprostinil crystal Form I has an X-ray powder diffraction (XRPD) pattern exhibiting its five strongest characteristic peaks at the following 2θ reflection angles: 3.3±0.2°, 6.6±0.2°, 14.2±0.2°, 18.9±0.2°, 21.3±0.2°, and 22.5±0.2°. In a preferred embodiment, the XRPD pattern of Hexadecyl Treprostinil crystal Form I further comprises characteristic peaks at the following 2θ reflection angles: 13.8±0.2°, 15.3±0.2°, 16.9±0.2°, 17.8±0.2°, 19.8±0.2°, 20.6±0.2°, 20.9±0.20, 24.4±0.2°, and 24.8±0.2°. More preferably, the XRPD pattern of Hexadecyl Treprostinil crystal Form I is consistent with FIG. 1. The particular data of Hexadecyl Treprostinil crystal Form I is shown in Table 1.

TABLE 1

| 2θ angle (°) | d value (Å) | relative intensity (%) |
| --- | --- | --- |
| 3.3 | 26.6 | 100.0 |
| 6.6 | 13.4 | 40.1 |
| 9.8 | 9.0 | 4.5 |
| 13.1 | 6.8 | 2.8 |
| 13.8 | 6.4 | 7.9 |
| 14.2 | 6.2 | 46.0 |
| 15.3 | 5.8 | 11.3 |
| 16.3 | 5.4 | 6.7 |
| 16.9 | 5.2 | 19.7 |
| 17.8 | 5.0 | 16.0 |
| 18.9 | 4.7 | 92.8 |
| 19.8 | 4.5 | 14.5 |
| 20.6 | 4.3 | 8.2 |
| 20.9 | 4.2 | 20.2 |
| 21.3 | 4.2 | 32.2 |
| 22.5 | 4.0 | 27.8 |
| 24.4 | 3.6 | 27.7 |
| 24.8 | 3.6 | 19.4 |
| 26.2 | 3.4 | 4.5 |
| 27.3 | 3.3 | 2.3 |
| 27.8 | 3.2 | 2.1 |
| 28.8 | 3.1 | 1.5 |

TABLE 1-continued

| 2θ angle (°) | d value (Å) | relative intensity (%) |
|---|---|---|
| 29.9 | 3.0 | 1.6 |
| 31.2 | 2.9 | 1.2 |
| 32.5 | 2.8 | 1.5 |
| 34.0 | 2.6 | 2.5 |
| 36.2 | 2.5 | 1.8 |
| 36.8 | 2.4 | 3.4 |
| 39.7 | 2.3 | 2.7 |

In one embodiment, the present invention provides a Hexadecyl Treprostinil crystal Form I having an XRPD pattern substantially as shown in FIG. 1.

Figure 2:
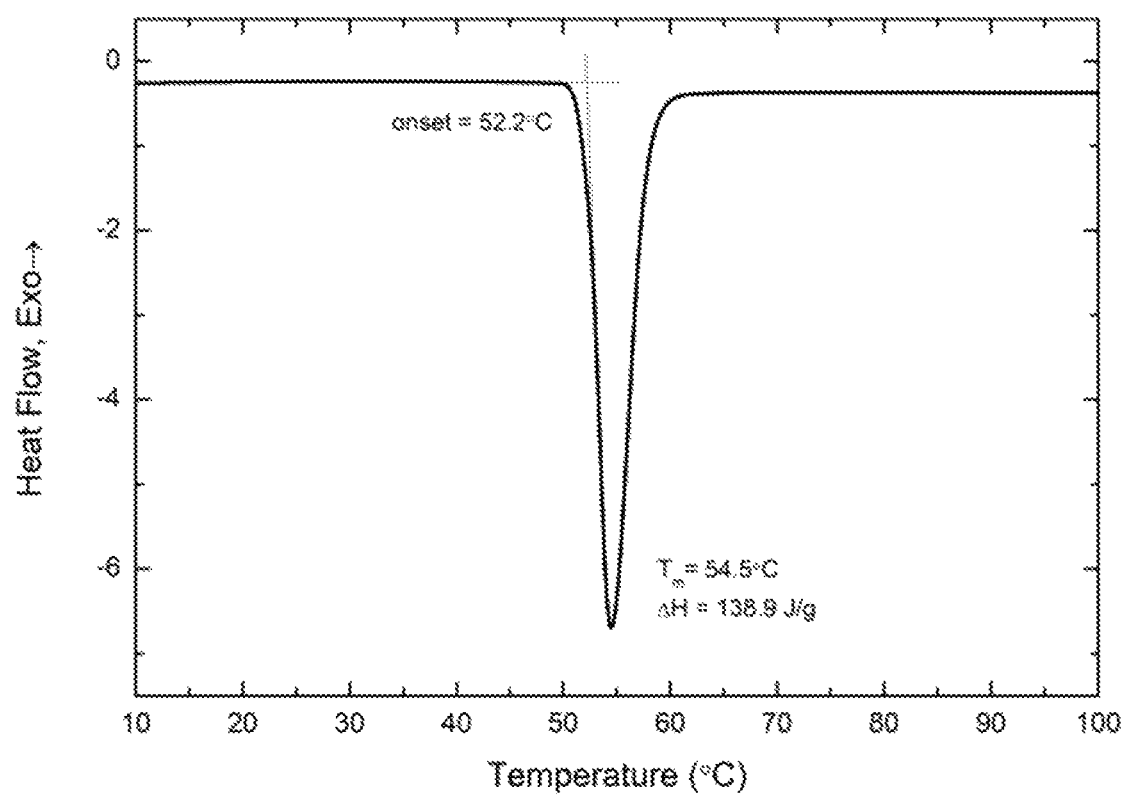
FIG. 2 shows a differential scanning calorimetry (DSC) thermogram pattern of Hexadecyl Treprostinil crystal Form I.

In one embodiment, the present invention provides a Hexadecyl Treprostinil crystal Form I having a differential scanning calorimetry (DSC) thermogram pattern comprising an endothermic peak with a peak onset temperature of approximately 52.2±1° C. and a peak maximum of approximately 54.5±1° C. In a preferred embodiment, the present invention provides a Hexadecyl Treprostinil crystal Form I having a DSC thermogram pattern substantially as shown in FIG. 2.

Figure 3:
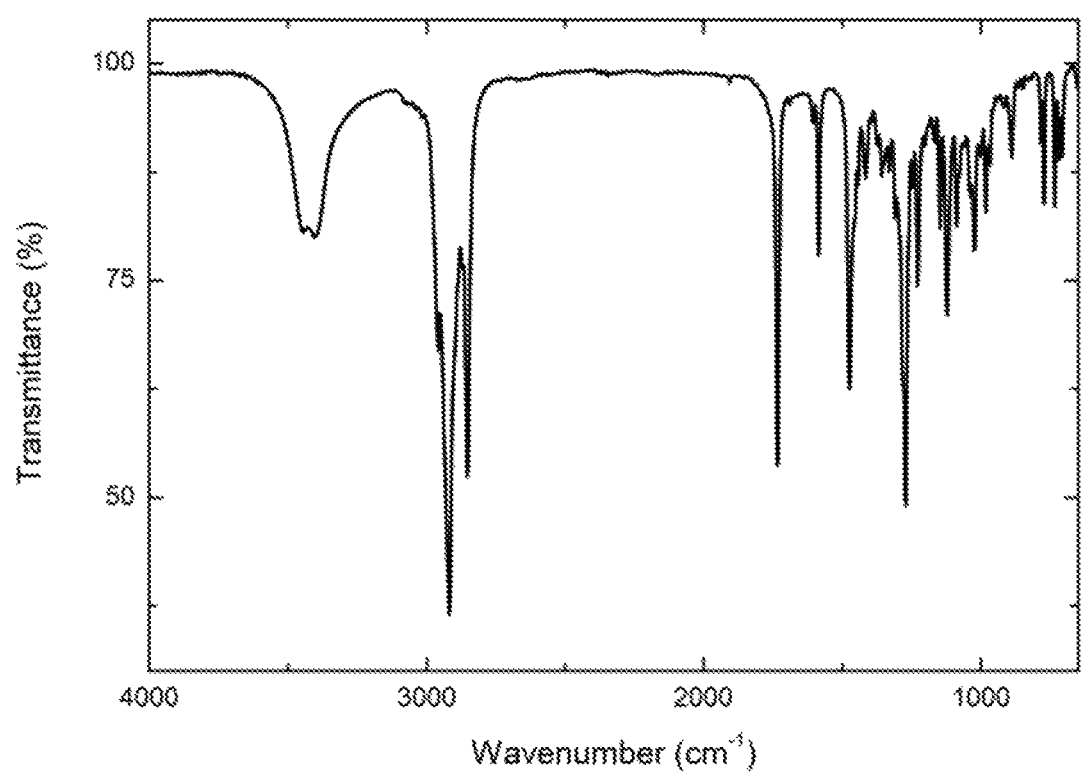
FIG. 3 shows a Fourier Transform Infrared (FTIR) spectrum of Hexadecyl Treprostinil crystal Form I.

In one embodiment, the present invention provides a Hexadecyl Treprostinil crystal Form I having a 1% KBr Fourier Transform Infrared (FTIR) spectrum comprising peaks, in terms of $cm^{-1}$, at $3445\pm4$ $cm^{-1}$, $3402\pm4$ $cm^{-1}$, $2958\pm4$ $cm^{-1}$, $2919\pm4$ $cm^{-1}$, $2871.4$ $cm^{-1}$, $2854\pm4$ $cm^{-1}$, $1733\pm4$ $cm^{-1}$, $1606\pm4$ $cm^{-1}$, $1585=4$ $cm^{-1}$, $1474\pm4$ $cm^{-1}$, $1443\pm4$ $cm^{-1}$, $1416.4$ $cm^{-1}$, $1374\pm4$ $cm^{-1}$, $1357\pm4$ $cm^{-1}$, $1331\pm4$ $cm^{-1}$, $1309\pm cm^{-1}$, $1271\pm4$ $cm^{-1}$, $1247\pm4$ $cm^{-1}$, $1229\pm4$ $cm^{-1}$, $120214$ $cm^{-1}$, $1167\pm4$ $cm^{-1}$, $1148\pm4$ $cm^{-1}$, $1122\pm4$ $cm^{-1}$, $1088\pm4$ $cm^{-1}$, $1039\pm4$ $cm^{-1}$, $1023\pm4$ $cm^{-1}$, $1000\pm4$ $cm^{-1}$, $982\pm4$ $cm^{-1}$, $968\pm4$ $cm^{-1}$, $917\pm4$ $cm^{-1}$, $889\pm4$ $cm^{-1}$, $784\pm4$ $cm^{-1}$, $772\pm4$ $cm^{-1}$, $7344$ $cm^{-1}$, $719\pm4$ $cm^{-1}$, $708\pm4$ $cm^{-1}$. In a preferred embodiment, the present invention provides a Hexadecyl Treprostinil crystal Form I having a 1% KBr FTIR spectrum substantially as shown in FIG. 3.

Due to the organic solvent system used in the method of the present invention, the precipitated Hexadecyl Treprostinil crystal Form I possesses compact solid characteristics and thus is easy to be filtered out. The residual solvents can be easily removed under high vacuum at room temperature. Moreover, the dried Hexadecyl Treprostinil crystal Form I with granular characteristics is much easier to weight for commercially handling comparing with the waxy solid form of Hexadecyl Treprostinil with high viscosity.

In addition, Hexadecyl Treprostinil crystal Form I is a stable crystalline form, which shows good stability, with no other crystalline forms or degraded products of impurities at room temperature for six months. Moreover, the assay of Hexadecyl Treprostinil crystal Form I can be kept between about 98.0% to about 102.0% even after thirty-six months of placement under normal storage temperature (about 5° C. to about −20° C.).

Hexadecyl Treprostinil Crystal Form II and Preparation Thereof

In an embodiment of the present invention, the method for preparing Hexadecyl Treprostinil crystal Form II comprises the steps of:

(a) dissolving crude Hexadecyl Treprostinil in a third solvent selected from the group consisting of ethyl ether, isopropyl ether, methyl tert-butyl ether, methyl isobutyl so ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution;

(b) lowering the temperature and/or adding a fourth solvent selected from the group consisting of pentane, hexane, heptane, octane, nonane, decane, cyclopentane, cyclohexane, cycloheptane, and mixtures thereof to the homogeneous solution;

(c) stirring until a precipitate is formed;

(d) filtering out the precipitate thereby isolating the Hexadecyl Treprostinil crystal Form II; and (e) optionally drying the Hexadecyl Treprostinil crystal Form II.

In the present invention, the third solvent used to dissolve the crude Hexadecyl Treprostinil is selected from the group consisting of ethyl ether, isopropyl ether, methyl ten-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof, preferably ethyl acetate and toluene. The volume of the third solvent depends on the types of the solvents used and may be about 0.5 ml to about 100 ml, preferably about 1 ml to about 50 ml, and more preferably about 2 ml to about 20 ml or about 1 ml to about 10 ml, per 1 g of the crude Hexadecyl Treprostinil. The crude Hexadecyl Treprostinil can be dissolved in the third solvent at a temperature ranging from about 0° C. to about 80° C., preferably from about 10° C. to about 60° C., and more preferably from room temperature to about 40° C.

In one embodiment of the present invention, the temperature of the homogenous solution is lowered to a temperature ranging from about −30° C. to about 50° C., preferably from about −20° C. to about 40° C., and more preferably from about −10° C. to about 30° C.

The selection of the fourth solvent is the key to determine whether a Hexadecyl Treprostinil crystal Form II can be formed. In a preferred embodiment, the volume of the fourth solvent selected from the group consisting of pentane, hexane, heptane, octane, nonane, decane, cyclopentane, cyclohexane, cycloheptane, and mixtures thereof depends on the types of the solvents used and may be about 0.5 ml to about 200 ml, about 1 ml to about 150 ml, or about 2 ml to about 100 ml, per 1 ml of so the third solvent. The fourth solvent can be added at a temperature ranging from about −30° C. to about 50° C., preferably from about −20° C. to about 40° C., and more preferably from about −10° C. to about 30° C.

In one embodiment of the present invention, the precipitation of the crystal may be performed at a temperature ranging from about −30° C. to about 50° C., preferably from about −20° C. to about 40° C., and more preferably from about −10° C. to about 30° C.

In one embodiment of the present invention, the step of filtering out the precipitate comprises using the fourth solvent or a mixture of the third solvent and the fourth solvent to wash the precipitate. In the mixing solvent, the ratio of the third solvent and the fourth solvent may be about 1:1 to about 1:100, preferably about 1:10 to about 1:50.

In one embodiment of the present invention, the Hexadecyl Treprostinil crystal Form II has an XRPD pattern exhibiting its six strongest characteristic peaks at the following 2θ reflection angles: 3.4±0.2°, 6.1±0.2°, 9.4±0.2°, 20.3±0.2°, 21.6±0.2°, and 23.4±0.2°. In a preferred embodiment, the XRPD pattern of Hexadecyl Treprostinil crystal Form II further comprises characteristic peaks at the following 2θ reflection angles: 7.0±0.2°, 9.0±0.2°, 12.2±0.2°, 12.7±0.2°, 17.5±0.2°, 18.0±0.2°, 18.5±0.2°, 19.1±0.2°, and 19.4±0.2°. More preferably, the XRPD pattern of Hexadecyl Treprostinil crystal Form II is consistent with FIG. 4. The particular data of Hexadecyl Treprostinil crystal Form II is shown in Table 2.

TABLE 2

| 2θ angle (°) | d value (Å) | relative intensity (%) |
|---|---|---|
| 3.4 | 26.0 | 100.0 |
| 4.5 | 19.6 | 2.2 |
| 6.1 | 14.5 | 45.1 |
| 7.0 | 12.6 | 22.0 |
| 7.7 | 11.5 | 3.9 |
| 9.0 | 9.8 | 27.8 |
| 9.4 | 9.4 | 85.5 |
| 10.0 | 8.8 | 3.6 |
| 10.6 | 8.3 | 13.9 |
| 17.2 | 7.7 | 22.6 |
| 12.7 | 7.0 | 29.9 |
| 13.9 | 6.4 | 3.8 |
| 14.2 | 6.2 | 3.9 |
| 14.9 | 5.9 | 5.2 |
| 15.5 | 5.7 | 17.2 |
| 16.1 | 5.5 | 18.1 |
| 16.7 | 5.3 | 6.2 |
| 17.5 | 5.1 | 25.4 |
| 18.0 | 4.9 | 30.8 |
| 18.5 | 4.8 | 79.3 |
| 19.1 | 4.6 | 33.8 |
| 19.4 | 4.6 | 30.3 |
| 20.3 | 4.4 | 39.9 |
| 20.9 | 4.2 | 19.8 |
| 71.6 | 4.1 | 40.6 |
| 22.6 | 3.9 | 9.4 |
| 23.4 | 3.8 | 81.9 |
| 25.4 | 3.5 | 9.3 |
| 27.7 | 3.2 | 3.6 |
| 28.8 | 3.1 | 3.1 |
| 30.9 | 2.9 | 2.3 |
| 37.3 | 2.4 | 2.1 |
| 40.0 | 2.3 | 2.8 |
| 43.3 | 2.1 | 2.1 |

Figure 4:
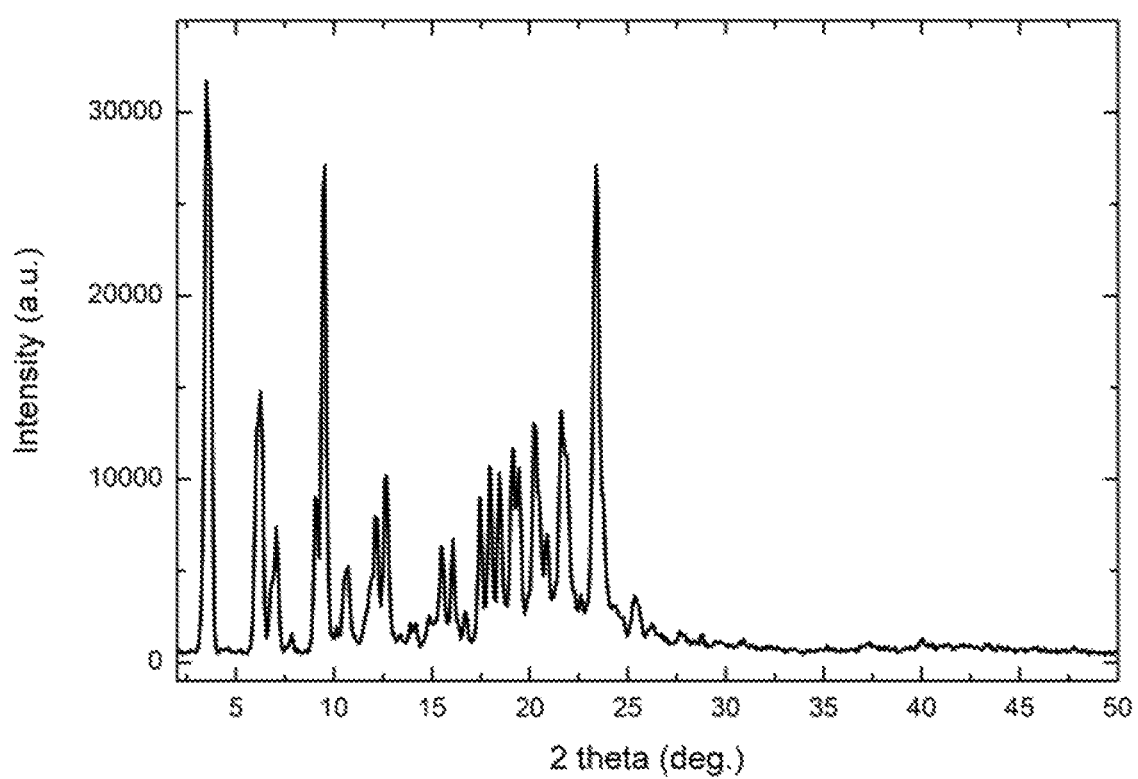
FIG. 4 shows an X-ray powder diffraction (XRPD) pattern of Hexadecyl Treprostinil crystal Form II.

In one embodiment, the present invention provides a Hexadecyl Treprostinil crystal Form II having an XRPD pattern substantially as shown in FIG. 4.

Figure 5:
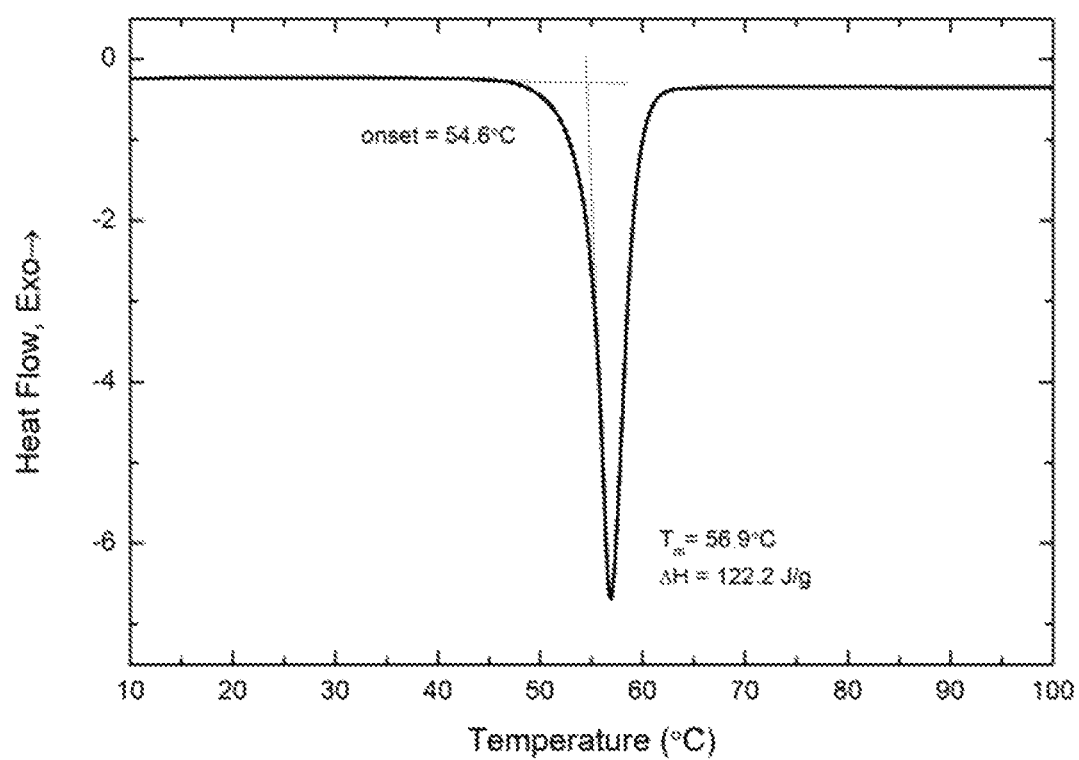
FIG. 5 shows a differential scanning calorimetry (DSC) thermogram pattern of Hexadecyl Treprostinil crystal Form II.

In one embodiment, the present invention provides a Hexadecyl Treprostinil crystal Form II having a DSC thermogram pattern comprising an endothermic peak with a peak onset temperature of approximately 54.6±1° C. and a peak maximum of approximately 56.9±1° C. In a preferred embodiment, the present invention provides a Hexadecyl Treprostinil crystal Form II having a DSC thermogram pattern substantially as shown in FIG. 5.

Figure 6:
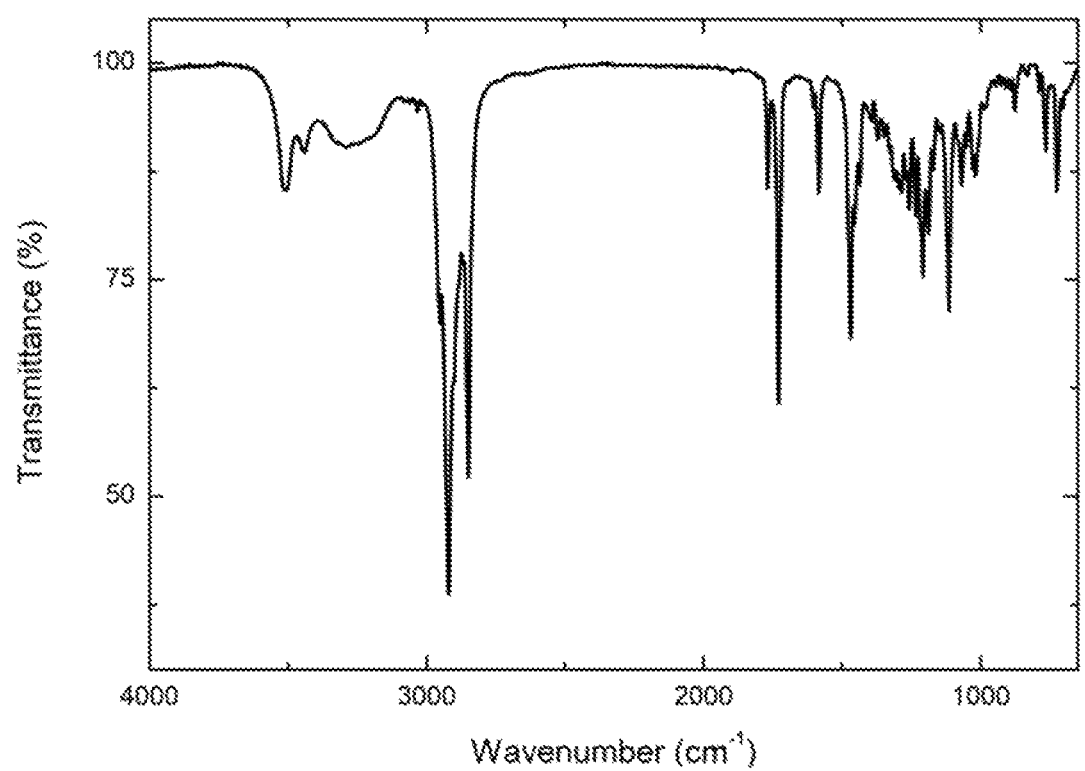
FIG. 6 shows a Fourier Transform Infrared (FTIR) spectrum of Hexadecyl Treprostinil crystal Form II.

In one embodiment, the present invention provides a Hexadecyl Treprostinil crystal Form II having a 1% KBr FTIR spectrum comprising peaks, in terms of $cm^{-1}$, at 3515±4 $cm^{-1}$, 3443±4 $cm^{-1}$, 3291±4 $cm^{-1}$, 3034±4 $cm^{-1}$, 29534 $cm^{-1}$, 2922±4 $cm^{-1}$, 2851±4 $cm^{-1}$, 1769±4 $cm^{-1}$, 1730±4 $cm^{-1}$, 1605±4 $cm^{-1}$, 1584±4 $cm^{-1}$, 1469±4 $cm^{-1}$, 1456±4 $cm^{-1}$, 1437±4 $cm^{-1}$, 1395±4 $cm^{-1}$, 1371±4 $cm^{-1}$, 347±4 $cm^{-1}$, 1330±4 $cm^{-1}$, 1311±4 $cm^{-1}$, 1295±4 $cm^{-1}$, 1286±4 $cm^{-1}$, 1271±4 $cm^{-1}$, 1259±4 $cm^{-1}$, 1235±4 $cm^{-1}$, 1218±4 $cm^{-1}$, 1209±4 $cm^{-1}$, 1189±4 $cm^{-1}$, 1171±4 $cm^{-1}$, 1148±4 $cm^{-1}$, 1115±4 $cm^{-1}$, 1070±4 $cm^{-1}$, 1053±4 $cm^{-1}$, 1030±4 $cm^{-1}$, 1019±4 $cm^{-1}$, 989±4 $cm^{-1}$, 946±4 $cm^{-1}$, 926±4 $cm^{-1}$, 9094 $cm^{-1}$, 893±4 $cm^{-1}$, 878±4 $cm^{-1}$, 790±4 $cm^{-1}$, 765±4 $cm^{-1}$, 726±4 $cm^{-1}$, 704±4 $cm^{-1}$. In a preferred embodiment, the present invention provides a Hexadecyl Treprostinil crystal Form II having a 1% KBr FTIR spectrum substantially as shown in FIG. 6.

Due to the organic solvent system used in the method of the present invention, the precipitated Hexadecyl Treprostinil crystal Form II possesses compact solid characteristics and thus is easy to be filtered out. The residual solvents can be easily removed under high vacuum at room temperature. Moreover, the dried Hexadecyl Treprostinil crystal Form II with granular characteristics is much easier to weight for commercially handling comparing with the waxy solid form of Hexadecyl Treprostinil with high viscosity.

In addition, Hexadecyl Treprostinil crystal Form II is a stable crystalline form, which shows good stability, with no other crystalline forms or degraded products of impurities at room temperature for six months. Moreover, the assay of Hexadecyl Treprostinil crystal Form II can be kept between about 98.0 to about 102.0% even after thirty-six months of placement under normal storage temperature (about 5° C. to about −2° C.).

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 20 to 50° with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC thermogram patterns were collected on a TA DISCOVERY DSC25 instrument. The samples (ca. 5 mg) were weighed into an aluminum pan with a crimping closed aluminum lid. The prepared samples were analyzed from 10° C. to 100° C. at scan rate of 10° C./min under a flow of nitrogen (ca. 50 ml/min). The melting temperature and heat of fusion were calibrated by indium (In) before measurement.

Fourier Transform Infrared (FTIR) Analysis: The FTIR spectra were collected on a Perkin Elmer SPECTRUM 100 instrument. The samples were mixed with potassium bromide (KBr) in an approximately 1:100 ratio (w/w) using an agate mortar and pestle. The mixture was compressed in a pellet die at a pressure of about 10 to 13 tonnes for 2 minutes. The resulting disk was scanned 4 times versus a collected background from 4000 $cm^{-1}$ to 650 $cm^{-1}$ at a resolution of 4 $cm^{-1}$. The data was baseline corrected and normalized.

Example 1

Preparation of Crude Hexadecyl Treprostinil 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetic acid (40.0 g, 102.4 mmol) was dissolved in 600 ml dimethylformamide and followed by addition of 42.0 g potassium carbonate with 72.0 g I-iodohexadecane, and stirred at 60° C. for 1 hour. Afterwards, the reaction mixture was slowly cooled to 10° C., and 650 ml water and 650 ml ethyl so acetate with 50.0 g magnesium sulfate were added to the reaction mixture for extraction. The extraction solution was evaporated off under vacuum at room temperature to get crude product. The crude product was then purified by chromatography on silica gel using a mixture of hexane and ethyl acetate as a gradient eluent to obtain 58.6 g off-white waxy solid (crude Hexadecyl Treprostinil).

Example 2

Preparation of Hexadecyl Treprostinil Crystal Form I

Crude Hexadecyl Treprostinil (1.00 g, from Example 1) and propanol (5 mil) were heated to 40° C. for dissolution and then cooled to room temperature. Water (5 ml) was added slowly dropwise and the mixture was stirred in ice water bath for 18 hours until solid precipitation occurred. Afterwards, the resulting suspension was filtered and rinsed, and then dried under high vacuum at room temperature for 24 hours to give 0.92 g Hexadecyl Treprostinil crystal Form I. The XRPD, DSC and FTIR results are the same as shown in FIG. 1, FIG. 2 and FIG. 3.

Example 3

Preparation of Hexadecyl Treprostinil Crystal Form I

Crude Hexadecyl Treprostinil (1.01 g, from Example 1) and ethanol (6 mil) were heated to 40° C. for dissolution and then cooled to room temperature. Acetonitrile (30 ml) was added slowly dropwise and the mixture was stirred in ice water bath for 18 hours until solid precipitation occurred. Afterwards, the resulting suspension was filtered and rinsed, and then dried under high vacuum at room temperature for 24 hours to give 0.90 g Hexadecyl Treprostinil crystal Form I. The XRPD, DSC and FTIR results are the same as shown in FIG. 1, FIG. 2 and FIG. 3.

Example 4

Preparation of Hexadecyl Treprostinil Crystal Form I

Crude Hexadecyl Treprostinil (1.0) g, from Example 1) and toluene (5 ml) were heated to 40° C. for dissolution. Acetonitrile (50 ml) was added slowly dropwise and the mixture was stirred in ice water bath for 20 hours until solid precipitation occurred. Afterwards, the resulting suspension was filtered and rinsed, and then dried under high vacuum at room temperature for 24 hours to give 0.91 g Hexadecyl Treprostinil crystal Form I. The XRPD, DSC and FTIR results are the same as shown in FIG. 1, FIG. 2 and FIG. 3.

Example 5

Preparation of Hexadecyl Treprostinil Crystal Form II

Crude Hexadecyl Treprostinil (1.01 g, from Example 1) and ethyl acetate (1 ml) were heated to 40° C. for dissolution and then cooled to room temperature. N-hexane (30 ml) was added slowly dropwise and the mixture was stirred in ice water bath for 18 hours until solid precipitation occurred. Afterwards, the resulting suspension was filtered and rinsed, and then dried under high vacuum at room temperature for 24 hours to give 0.88 g Hexadecyl Treprostinil crystal Form II. The XRPD, DSC and FTIR results are the same as shown in FIG. 4, FIG. 5 and FIG. 6.

Example 6

Preparation of Hexadecyl Treprostinil Crystal Form II

Crude Hexadecyl Treprostinil (1.00 g, from Example 1) and toluene (3 ml) were heated to 40° C. for dissolution and then cooled to room temperature. N-heptane (40 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.85 g Hexadecyl Treprostinil crystal Form II. The XRPD, DSC and FTIR results are the same as shown in FIG. 4, FIG. 5 and FIG. 6.

Example 7

Preparation of Hexadecyl Treprostinil Crystal Form II

Crude Hexadecyl Treprostinil (1.01 g, from Example 1) and methyl tert-butyl ether (3 ml) were heated to 40° C. for dissolution. N-pentane (30 ml) was added slowly dropwise and the mixture was stirred in ice water bath for 18 hours until solid precipitation occurred. Afterwards, the resulting suspension was filtered and rinsed, and then dried under high vacuum at room temperature for 24 hours to give 0.85 g Hexadecyl Treprostinil crystal Form II. The XRPD, DSC and FTR results are the same as shown in FIG. 4, FIG. 5 and FIG. 6.

What is claimed is:

1. A crystalline Form I of Hexadecyl Treprostinil, characterized by having an X-ray powder diffraction (XRPD) pattern comprising its six strongest characteristic peaks at the following 2θ reflection angles: 3.3±0.2°, 6.6±0.2°, 14.2±0.2°, 18.9±0.2°, 21.3±0.2°, and 22.5±0.2°.

2. The crystalline Form I of Hexadecyl Treprostinil of claim 1, wherein the XRPD pattern further comprises characteristic peaks at the following 2θ reflection angles: 13.8±0.2°, 15.3±0.2°, 16.9±0.2°, 17.8±0.2°, 19.8±0.2°, 20.6±0.2°, 20.9±0.2°, 24.4±0.2°, and 24.8±0.2°.

3. The crystalline Form I of Hexadecyl Treprostinil of claim 1, wherein the XRPD pattern is substantially shown in FIG. 1.

4. The crystalline Form I of Hexadecyl Treprostinil of claim 1, further having a differential scanning calorimetry (DSC) thermogram pattern comprising an endothermic peak with a peak onset temperature of approximately 52.2±1° C. and a peak maximum of approximately 54.5±1° C.

5. The crystalline Form I of Hexadecyl Treprostinil of claim 4, wherein the DSC thermogram pattern is substantially shown in FIG. 2.

6. The crystalline Form I of Hexadecyl Treprostinil of claim 1, further having a 1% KBr Fourier transform infrared (FTIR) spectrum comprising peaks, in terms of $cm^{-1}$, at 3445±4 $cm^{-1}$, 3402±4 $cm^{-1}$, 2958±4 $cm^{-1}$, 2919±4 $cm^{-1}$, 2871±4 $cm^{-1}$, 2854±4 $cm^{-1}$, 1733±4 $cm^{-1}$, 1606±4 $cm^{-1}$, 1585±4 $cm^{-1}$, 1474±4 $cm^{-1}$, 1443±4 $cm^{-1}$, 1416±4 $cm^{-1}$, 1374±4 $cm^{-1}$, 1357±4 $cm^{-1}$, 1331±4 $cm^{-1}$, 1309±4 $cm^{-1}$, 1271±4 $cm^{-1}$, 1247±4 $cm^{-1}$, 1229±4 $cm^{-1}$, 1202±4 $cm^{-1}$, 1167±4 $cm^{-1}$, 1148±4 $cm^{-1}$, 1122±4 $cm^{-1}$, 1088±4 $cm^{-1}$, 1039±4 $cm^{-1}$, 1023±4 $cm^{-1}$, 1000±4 $cm^{-1}$, 982±4 $cm^{-1}$, 968±4 $cm^{-1}$, 917±4 $cm^{-1}$, 889±4 $cm^{-1}$, 784±4 $cm^{-1}$, 7724 $cm^{-1}$, 734±4 $cm^{-1}$, 719±4 $cm^{-1}$, 708±4 $cm^{-1}$.

7. The crystalline Form I of Hexadecyl Treprostinil of claim 6, wherein the FTIR spectrum is substantially shown in FIG. 3.

8. A method for preparing the crystalline Form I of Hexadecyl Treprostinil according to claim 1, which comprises the steps of:

dissolving Hexadecyl Treprostinil in a first solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution, lowering the temperature and/or adding a second solvent selected from the group consisting of acetonitrile, water, and mixtures thereof to the homogenous solution; and stirring until a precipitate is formed.

9. The method of claim 8, further comprising the steps of:

adding the second solvent or a mixture of the first solvent and the second solvent for rinsing the precipitate;

filtering out the precipitate thereby isolating the crystalline Form I of Hexadecyl Treprostinil; and optionally drying the crystalline Form I of Hexadecyl Treprostinil.

10. A crystalline Form II of Hexadecyl Treprostinil, characterized by having an XRPD pattern comprising its six strongest characteristic peaks at the following 2θ reflection angles: 3.4±0.2°, 6.1±0.2°, 9.4±0.2°, 20.3±0.2°, 21.6±0.2°, and 23.4±0.2°.

11. The crystalline Form II of Hexadecyl Treprostinil of claim 10, wherein the XRPD pattern further comprises characteristic peaks at the following 2θ reflection angles: 7.0±0.2°, 9.0±0.2°, 12.2±0.2°, 12.7±0.2°, 17.5±0.2°, 18.0±0.2°, 18.5±0.2°, 19.1±0.2°, and 19.4±0.2°.

12. The crystalline Form II of Hexadecyl Treprostinil of claim 10, wherein the XRPD pattern is substantially shown in FIG. 4.

13. The crystalline Form II of Hexadecyl Treprostinil of claim 10, further having a DSC thermogram pattern comprising an endothermic peak with a peak onset temperature of approximately 54.6±1° C. and a peak maximum of approximately 56.9±1° C.

14. The crystalline Form II of Hexadecyl Treprostinil of claim 13, wherein the DSC thermogram pattern is substantially shown in FIG. 5.

15. The crystalline Form II of Hexadecyl Treprostinil of claim 10, further having a 1% KBr FTIR spectrum comprising peaks, in terms of $cm^{-1}$, at 3515±4 $cm^{-1}$, 3443±4 $cm^{-1}$, 3291±4 $cm^{-1}$, 3034±4 $cm^{-1}$, 2953±4 $cm^{-1}$, 2922±4 $cm^{-1}$, 2851±4 $cm^{-1}$, 1769±4 $cm^{-1}$, 1730±4 $cm^{-1}$, 1605±4 $cm^{-1}$, 1584±4 $cm^{-1}$, 1469±4 $cm^{-1}$, 1456±4 $cm^{-1}$, 1437±4 $cm^{-1}$, 1395±4 $cm^{-1}$, 1371±4 $cm^{-1}$, 1347±4 $cm^{-1}$, 1330±4 $cm^{-1}$, 1311±4 $cm^{-1}$, 1295±4 $cm^{-1}$, 1286±4 $cm^{-1}$, 1271±4 $cm^{-1}$, 1259±4 $cm^{-1}$, 1235±4 $cm^{-1}$, 1218±4 $cm^{-1}$, 1209±4 $cm^{-1}$, 1189±4 $cm^{-1}$, 1171±4 $cm^{-1}$, 1148±4 $cm^{-1}$, 1115±4 $cm^{-1}$, 1070±4 $cm^{-1}$, 1053±4 $cm^{-1}$, 1030±4 $cm^{-1}$, 1019±4 $cm^{-1}$, 989±4 $cm^{-1}$, 946±4 $cm^{-1}$, 926±4 $cm^{-1}$, 909±4 $cm^{-1}$, 893±4 $cm^{-1}$, 878±4 $cm^{-1}$, 790±4 $cm^{-1}$, 765±4 $cm^{-1}$, 726±4 $cm^{-1}$, 704±4 $cm^{-1}$.

16. The crystalline Form II of Hexadecyl Treprostinil of claim 15, wherein the FTIR spectrum is substantially shown in FIG. 6.

17. A method for preparing the crystalline Form II of Hexadecyl Treprostinil according to claim 10, which comprises the steps of:

dissolving Hexadecyl Treprostinil in a third solvent selected from the group consisting of ethyl ether, isopropyl ether, methyl tert-butyl ether, methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof to form a homogenous solution;

lowering the temperature and/or adding a fourth solvent selected from the group consisting of pentane, hexane, heptane, octane, nonane, decane, cyclopentane, cyclohexane, cycloheptane, and mixtures thereof to the homogenous solution; and stirring until a precipitate is formed.

18. The method of claim 17, further comprising the steps of:

adding the fourth solvent or a mixture of the third solvent and the fourth solvent for rinsing the precipitate;

filtering out the precipitate thereby isolating the crystalline Form II of Hexadecyl Treprostinil; and optionally drying the crystalline Form II of Hexadecyl Treprostinil.

* * * * *